United States Patent [19]

Tantram et al.

[11] 4,132,616

[45] Jan. 2, 1979

[54] GAS SENSOR

[75] Inventors: Anthony D. S. Tantram, Great Bookham; Michael J. Kent, Leighton Buzzard; Alan G. Palmer, Teddington, all of England

[73] Assignee: City Technology Limited, London, England

[21] Appl. No.: 775,559

[22] Filed: Mar. 8, 1977

[30] Foreign Application Priority Data

Mar. 11, 1976 [GB] United Kingdom .............. 9843/76

[51] Int. Cl.² ........................................... G01N 27/46
[52] U.S. Cl. ............................. 204/195 P; 204/195 R
[58] Field of Search ............... 204/1 P, 195 P, 195 R; 324/29

[56] References Cited

U.S. PATENT DOCUMENTS

| | | | |
|---|---|---|---|
| 3,411,073 | 11/1968 | Marr | 324/33 |
| 3,787,308 | 1/1974 | Malaspina et al. | 204/195 P |
| 3,820,015 | 6/1974 | Jeunehomme | 324/33 |
| 3,857,771 | 12/1974 | Sternberg | 204/195 P X |

Primary Examiner—G. L. Kaplan
Attorney, Agent, or Firm—David A. Burge Co.

[57] ABSTRACT

An electro-chemical sensor for the measurement of concentrations of gas or vapor in accordance with the limiting current principle and comprising an electrolytic cell having a sensing electrode, a counter electrode and an intervening body of electrolyte and also a restriction to the rate of access of gas or vapor to the sensing electrode. The improvement comprises said restriction being in the form of a gas-phase diffusion barrier including at least one narrow passage for the diffusion of gas. The gas-phase diffusion barrier may be in the form of a porous body, of which the permeability of the body may be more than twenty times greater than the diffusibility, but is preferably less than ten times the diffusibility and more preferably not more than 10% greater than the diffusibility. Alternatively the gas-phase diffusion barrier may be defined by a capillary. The capillary may be of plastics material and may be enclosed within an outer metal sheath of lesser co-efficient of expansion. The capillary may be connected in series with a porous body.

12 Claims, 7 Drawing Figures

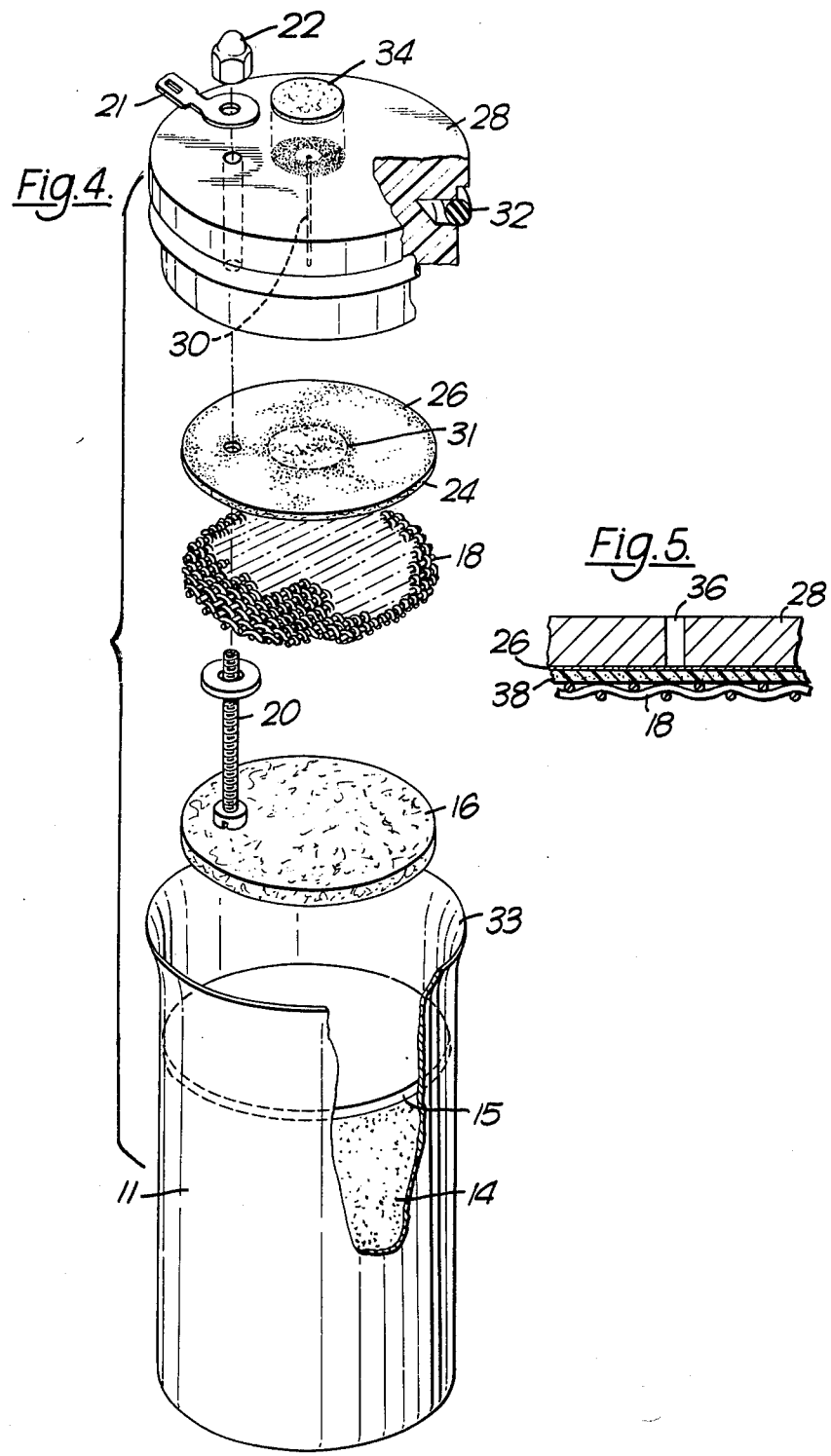

GAS SENSOR

This invention relates to electro-chemical gas sensors in which the gas or vapour to be sensed is caused to react at one electrode of an electro-chemical cell, which also includes a counter electrode and an intervening body of electrolyte, in such a way that the current through the cell is a function of the partial pressure of the gas or vapour to be sensed. The principle will be described in relation to the sensing of oxygen although it is to be understood that it is applicable to any gas or vapour which can be electro-chemically reacted in this way. Gases or vapours such as, for example, oxygen and nitrogen oxides which are electro-chemically reducible, are sensed at the cathode, while those which are electro-chemically oxidisible, such as carbon monoxide, sulphur dioxide and hydrogen sulphide are sensed at the anode.

In practice oxygen is electro-chemically reduced at an oxygen cathode, to which the rate of access of oxygen is restricted, for example by a diffusion barrier, under conditions such that the electrode is operating in the so-called limiting current region, illustrated by the shaded area of FIG. 1 of the accompanying drawings, which is a graph of current density plotted against polarizing potential and represents a typical oxygen-electrode polarization curve in which the limiting current is indicated as $i_L$. Under limiting current conditions the concentration of oxygen at the electrode surface is essentially zero. The limiting current, $i_L$ will then be proportional to the flux of oxygen, which will be a function of the partial pressure of oxygen in the gas being sensed. The relation between the partial pressure of oxygen and the flux of oxygen and hence the limiting current will be determined by the laws governing the permeation of oxygen across the diffusion barrier. To complete the sensing cell it is provided with an electrolyte and a counter electrode i.e., an anode, at which an oxidation reaction will occur.

The choice of anode material and mode of operation of an oxygen sensor of this type may be considered against the background of the curve shown in FIG. 1. The oxygen electrode must be polarised sufficiently to be well within the limiting current region, where the value of the limiting current is insensitive to potential, but it must not be polarised below the hydrogen potential where it can evolve hydrogen giving a false reading and problems with hydrogen gas bubbles. If the anode material is chosen so that its operating potential is within the shaded region of FIG. 1, then sufficient volts are available for the sensor to be self-powered and it can be operated simply with a suitable load resistor between anode and cathode, the current being measured with a volt meter.

If the anode has an operating potential above the shaded region, then an external power source will be required to polarise the oxygen cathode sufficiently into the limiting current region. The applied voltage must be kept below the value that would polarise the cathode into the hydrogen evolution region. The use of an anode material with an operating potential below the shaded region is to be avoided, since firstly a constant voltage load circuit is required to keep the cathode potential in the required safe region and secondly an anode is liable to self-discharge with the production of hydrogen if the sensor is on open circuit. If the gas to be sensed is a reducing gas parallel considerations apply, but here the sensing electrode is now the anode, which should be polarised well into the limiting current region, but not so far that the oxygen evolution potential is reached.

Known types of gas sensors working on these general principles achieve the necessary restriction to the access of gas to the sensing electrode by the provision of a solid membrane between the body of the gas to be tested and the sensing electrode so that the flux of gas is restricted by the diffusion rate of gas in solution in the solid membrane. Examples of such solid membranes that have been used are films of polytetrafluoroethylene, polyethylene and silicone rubber. An example of a sensor using such a membrane is that described in S.M.R.E. Digest. Gas Detection 1. 1972.

The use of solid membrane films has the disadvantages that very thin membranes have to be used to achieve practical current levels and more importantly that the resulting sensor has an extremely high temperature co-efficient, which may be as high as 2% to 3% per degree centigrade. This means that provision must be made for temperature compensation and this is difficult to achieve accurately and reliably. This high temperature coefficient is a fundamental consequence of the process of transporting gas in solution through a solid material, being associated with the high activation energy required for this purpose.

According to the present invention a sensor of the type just described, operating on the limiting current principle for the detection of oxygen or other gas or vapour includes a gas phase diffusion barrier, that is to say a barrier through which the significant transport process to provide the necessary controlled restriction to the access of gas to the sensing electrode is one of gaseous diffusion rather than of diffusion of the gas in solution. For this purpose, one or more narrow gas passages need to be provided through an otherwise solid barrier and the barrier may thus be either in the form of a porous sheet, plug or membrane or in the form of a simple capillary tube or a combination of these two alternatives arranged in series with one another.

We have found that with a barrier of this type diffusion and the resulting sensor signal varies so little with temperature that, for many practical purposes, no temperature compensation is necessary, so that the arrangement as a whole is thus simplified and greater accuracy and reliability results.

We have also found that with a barrier of this type the sensor measures composition, e.g. percentage oxygen in the gas, and that the resulting sensor signal at a given composition is independent of pressure. This is clearly an important advantage in any application where variations in pressure can occur and a measure of gas composition is required.

If the gas phase diffusion barrier has pores of sufficiently large size some gas transport may occur by bulk flow as well as by diffusion. The effect of this is to result in a non-linear variation of signal with composition. The non-linearity becomes increasingly noticeable as the percentage of the gas being measured (e.g. oxygen) rises above about 20%. Explanation for this effect can be found in Principles of Unit Operations. John Wiley and Sons Inc., 1966, page 118.

For many purposes this is not of practical importance, but may lead to difficulties when high concentrations need to be measured. Moreover, the bulk flow effect can also lead to the sensor signal being sensitive to draughts and modulations to the ambient pressure.

Preferably, therefore, these bulk flow effects are substantially eliminated by the use of porous membranes of limited pore size. To prevent any appreciable bulk flow the equivalent pore size needs to be not greater than 1 micrometer and preferably appreciably lower than this, i.e., as low as or lower than 0.3 micrometers to 0.03 micrometers. Any particular porous body will have a range of pore sizes and pore shapes and a variation of pore shapes through the thickness of the body. As a consequence, the limitation of pore size is best determined in terms of the limitation of bulk flow effects. A guide to this can be obtained as a relationship between the permeability (bulk flow plus diffusion) and diffusibility (diffusion only). A restriction which is adequate to avoid any major effects of draughts is obtained if the former is not more than twenty times as great as the latter, while to eliminate the effect of draughts altogether, the permeability needs to be less than ten times as great as the diffusibility. To obtain effective linearity the requirement is considerably more stringent and for this purpose the permeability should not exceed the diffusibility by more than 10%.

Examples of commercially available porous membrane materials whose use will effectively eliminate the bulk flow effect are some grades of porous "unsintered" polytetrafluorethylene tape and porous polycarbonate films available commercially under the Trade names "Nuclepore", "Unipore", "Millipore".

It can be predicted theoretically and confirmed experimentally that when using a gas-phase diffusion barrier as so far described, there will still be a very small residual temperature co-efficient. If the barrier is defined by a capillary, even this small co-efficient can be virtually eliminated if the capillary is of plastics material and is enclosed within an outer metal sheath of lesser co-efficient of expansion. If, for example, the temperature rises the plastics material expands more than the constraining metal tube so that the capillary passage through the plastics tube tends to constrict and lengthen. Thus, for example, with the use of a 5 mm long vinyl capillary (temperature co-efficient of expansion about $70 \times 10^{-6}$ per degree centigrade) of 3 mm outside diameter and 0.25 mm bore, mounted in a stainless steel outer tube (temperature co-efficient of expansion about $10 \times 10^{-6}$ per degree centigrade), the differential expansion effect will almost exactly compensate for a 0.17 per cent per degree centigrade temperature co-efficient. Although this represents a valuable refinement, accuracy of this order is not often required and this form of construction will not be described in further detail.

In sensors of the type described the operating life is governed primarily by the amount of counter electrode material (anode in the case of the oxygen sensor) in the cell and the total cell current. In the interests of long life and small size it is therefore worthwhile to reduce the total cell current as far as practical, a value of less than 10 mA usually being desirable. As a guide the total current for an oxygen sensor with a porous membrane operating in ambient air will be given approximately by $i_L = 0.76\, A\theta/\tau L$ where $i_L$ is the total sensor current in amps.

A is the area in $cm^2$
$\theta$ is the fractional porosity
$\tau$ is the tortuosity factor
L is the thickness in cm Undue increases in the values of $\tau$ and L adversely affect the response time, so that attention needs to be directed to the values of A and $\theta$. In the case of a Nuclepore membrane, the manufacturing process is such that the porosity of the membrane can be controlled over a fairly wide range, but in other cases, such as with commercially available porous unsintered PTFE, the porosity is inconveniently high. In such cases, it is possible to reduce the total porosity by selective filling of the pores, for example by successive impregnations with solutions of wax or resins, but this leads to difficulty in obtaining even properties over the whole effective area of membrane.

With a porous unsintered PTFE membrane a preferred way of reducing porosity is by pre-pressing the membrane before assembly into the sensor. We have found that a pressure of about 2.5 tons per square inch is suitable.

Details of this and of other factors involved and of electro-chemical sensors in accordance with the invention will now be described, by way of example, with reference to FIGS. 2 to 7 of the accompanying drawings, in which:

FIG. 4 is an exploded perspective view of one construction of detector cell in accordance with the invention;

FIG. 5 is a detailed cross sectional view showing part of a modification of the construction of FIG. 4;

Figure 2:
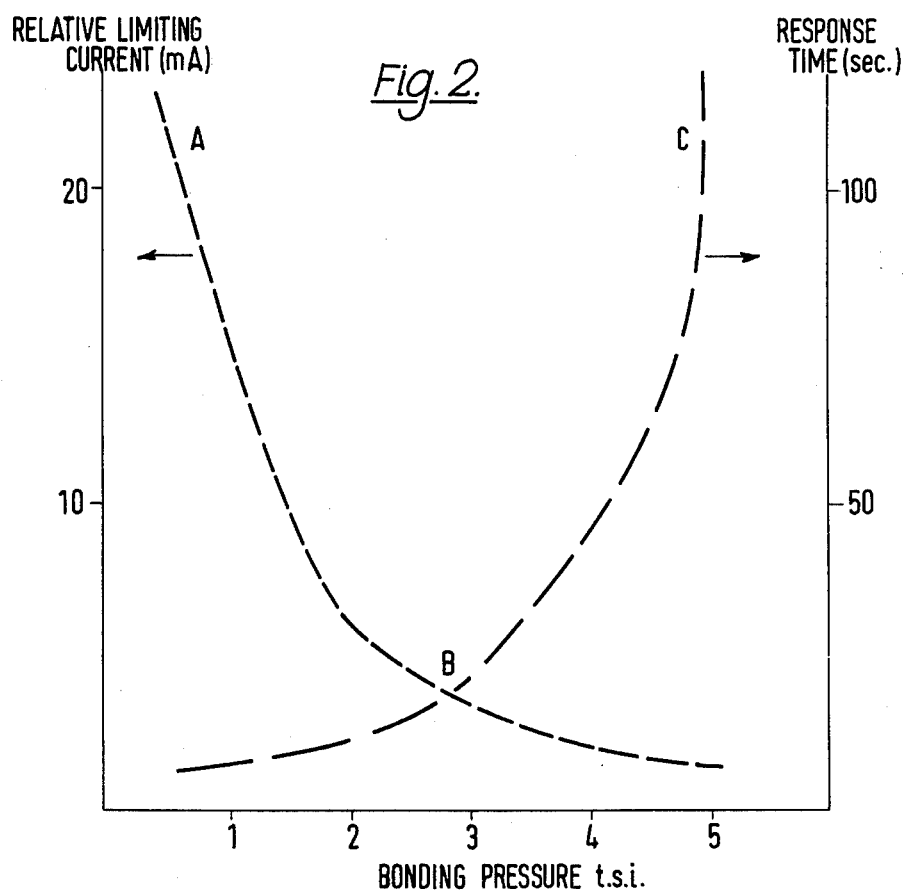
FIG. 2 is a graph in which the sensor current and response time are plotted against pressing pressure.

FIG. 2 shows the effect of pressing pressure on sensor current and response time when using an 0.008 inch thick PTFE tape which has an initial porosity of about 26%, as supplied by W. L. Gore and Associates (UK) Limited, for cable insulation. As can be seen, higher pressing pressures will tend to unduly extend the response time of the resulting sensor. To ensure a suitably low current from the sensor it is still necessary to restrict the diffusion area and, for example, a commercially available porous PTFE tape pressed as described above should be masked to limit the diffusion area to the equivalent of 1 to 1.5 millimeters diameter to reduce the sensor current to the order of 1 to 2 mA/cm ambient air.

The use of a pressed porous PTFE membrane in the manner described effectively eliminates bulk flow and sensors made in this way have given a linear response up to 100% oxygen.

If the gas phase diffusion barrier takes the form of a capillary then this can be made to provide the controlling restriction to diffusion. As a guide to the choice of capillary size the current on ambient air will be approximately 0.6 $d^2/L$ amps where d and L are the diameter and length of the capillary respectively in centimeters. Moreover, it is found that the response time of the sensor increases with the length of capillary used, so that in choosing a suitable combination of d and L for any specific purpose, this factor needs to be taken into account.

Figure 3:
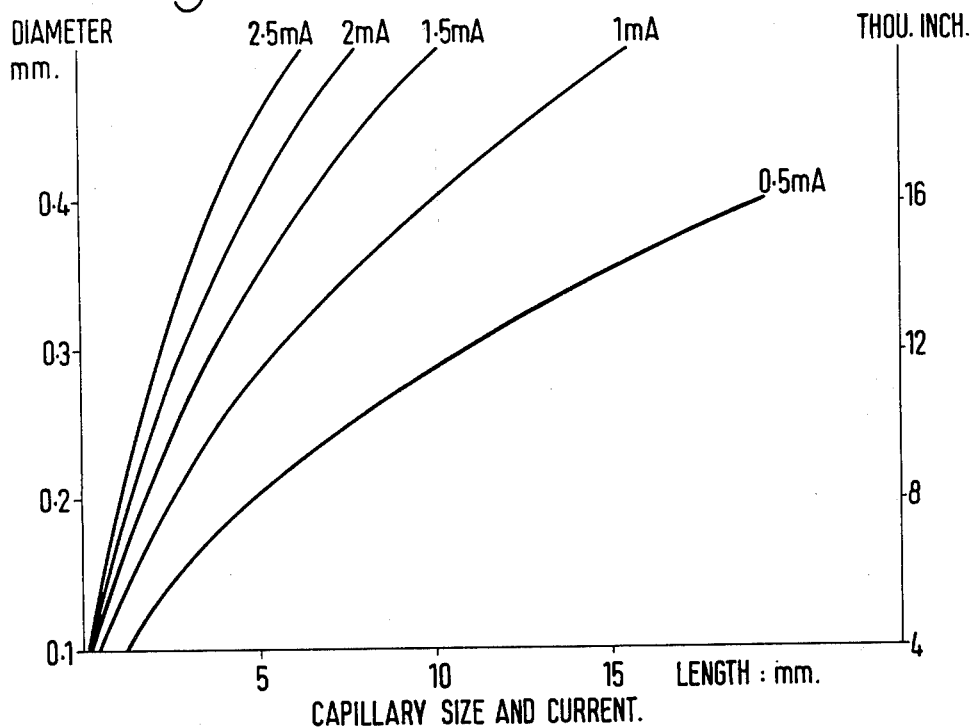
FIG. 3 is a graph in which capillary length and sensor current are plotted against capillary diameter.

FIG. 3 shows the effect of variations in length and diameter of the capillary as a function of sensor current. Whatever the proportions of the capillary, it is preferable to include a low pore size membrane in series with the capillary in order to reduce the bulk flow effect discussed earlier. If a very short capillary is used, it might normally be regarded as constituting a narrow orifice or jet. For present purposes, however, the term "capillary" is used, regardless of the length.

Although the parameters are quoted in terms of a capillary of circular cross section, capillaries of other cross sectional shapes may be used, and it is not essential for the cross sectional shape and area to be constant throughout the length of capillary. Neither is it essential for the capillary to be straight: it can, for example, contain bends or be coiled or folded.

These size considerations have been discussed in the context of operation around normal oxygen concentrations in air. For the measurement of low concentrations of gas the masking hole and capillary sizes may be altered to result in a signal of appropriate level for the application.

The sensing electrode, the cathode in the case of an oxygen sensor, should have sufficient activity that it does not itself constitute a limitation to the current, this limitation being controlled by the porous membrane and/or the capillary where this is incorporated. There are many examples of active oxygen electrodes that have been developed for fuel cells and metal-air batteries. A suitable cathode may be readily made by mixing a finely divided catalyst such as platinum, silver, silverised graphite or high surface area graphite with PTFE suspension and applying this to a suitable current collector such as a nickel gauze, followed by a drying and curing treatment. In order to ensure that there is no seepage of electrolyte through the electrode it is desirable to apply a further layer of porous hydrophobic material, such as PTFE, to the gas side of the electrode. Where the porous diffusion barrier membrane is itself hydrophobic, for example when it is porous PTFE, this will serve as the waterproofing layer if it is pressed directly on to the electrode.

In other cases it is desirable to mount the porous membrane separately from the electrode with a gap between the two, for example if the membrane is Nuclepore, which is hydrophilic, or for reasons of easier fabrication.

Similarly when a capillary is used it is preferable to have a shallow cavity, or relatively larger area than the cross sectional area of the capillary between the inner end of the capillary and the electrode. This enables the current to be spread over sufficient electrode area to result in a low current density that will not produce limiting effects at the electrode itself.

Suitable electolytes for use in the sensor include potassium hydroxide, potassium carbonate, sodium hydroxide, potassium phosphate, potassium citrate and potassium borate. The electrolyte may be mixed with a gelling agent such as carboxy methyl cellulose.

Figure 1:
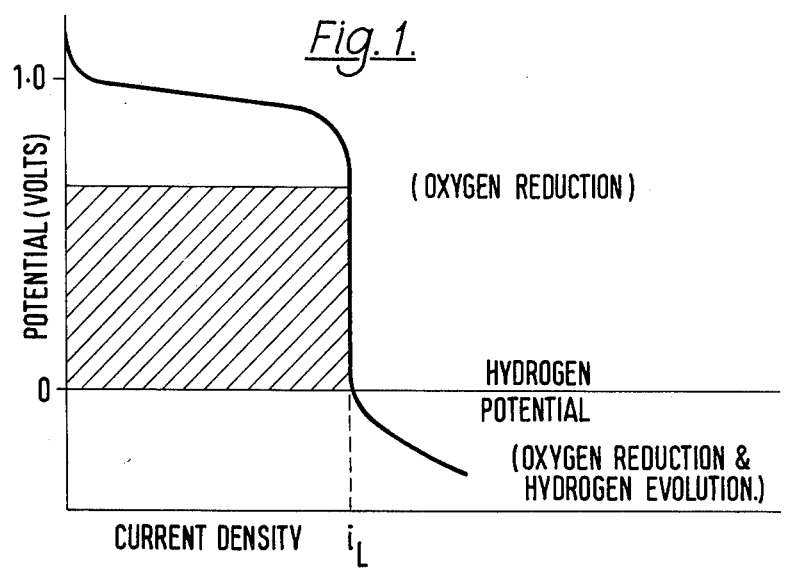

Most of the factors governing the choice of anode materials for an oxygen sensor in accordance with the invention are the same as were discussed earlier. Preferred materials with potentials in the shaded region of FIG. 1 include cadmium, lead, bismuth and copper. The anode material may be in any suitable form such as foil, corrugated or perforated foil, mesh, pressed powder or it may be plated on to a foil or mesh current collector. When the metal to be used is lead, this may conveniently be in the form of lead wool. A particular advantage can be obtained with cadmium plated from a fluoroborate bath containing caffeine, resorcinol and pepsin as additives. Such anode when used in an oxygen sensor in accordance with the invention and with potassium carbonate electrolyte may achieve utilisations of the cadmium of close to 100%.

If the anode material, such as lead or cadmium, is plated on to a metal, which is more noble, such as copper, then an additional advantage can be obtained, namely to make possible a check on the state of discharge of the sensor. When the plated material is exhausted the open circuit voltage of the sensor will drop appreciably, so that this stage may be checked by measurement. The sensor will, however, continue to function since the copper will now function as the anode material.

Sensors in accordance with the invention may be constructed in a variety of shapes and sizes to best fit the application concerned. For example the sensors may be made in a cylindrical shape like a conventional primary battery with the membrane and sensing electrode at one end, or they may be made in an annular or "wraparound" design, in which the membrane and sensing electrode are attached to an inner tube, around which is an annular container holding the electrolyte and counter electrode. An annular design is particularly suitable for incorporation in a flow system.

FIG. 4 is an exploded perspective view of one form of oxygen sensor in accordance with the invention. The cell is contained within a nickel-plated can 11, the bottom portion of which holds an anode 14 constituted by granulated lead and potassium carbonate electrolyte of sufficient volume to have a free surface at 15 just above the surface of the anode.

A fibrous disc 16 which is fitted immediately above the surface of the electrolyte acts as a wicking separator and contacts the cathode of the cell 18, which operates as the oxygen electrode. The cathode consists of nickel gauze covered with a paste of silverised graphite catalyst. A small bolt 20 extends upwardly from the cathode 18 and through the superimposed components to a terminal tag 21 constituting the cathode connection of the cell, this tag being held in position by a nut 22.

The cathode is waterproofed by a layer 24 of unsintered porous PTFE tape pressed into contact with the electrode to form a unitary assembly. This assembly is secured by an adhesive seal 26 to an end cap 28 formed with a capillary 30. The construction is such as to leave a narrow gap between the inner end of the capillary 30 and the top of the electrode assembly, as indicated by the circle 31. The end cap is provided with an O-ring 32 which fits into the flared mouth 33 of the can 11 so as to form a tight sealing fit. Finally, the outer end of the capillary 30 is covered by a porous PTFE membrane 34 glued to the upper surface of the end cap 28 in order to reduce transport of oxygen by bulk flow. The nickel-plated can 11 constitutes the anode connection and, in use, the cell is loaded with a resistor to bring the sensor current into the limiting current region.

FIG. 5 which is a detailed view to an enlarged scale shows, in cross section, the central portion of an alternative form of end cap. As can be seen, this end cap, also identified as 28, has a relatively large central hole 36, e.g. of 1 mm diameter, rather than a capillary, this hole merely serving as a mask to limit the effective area of the diffusion barrier which is constituted by a porous PTFE membrane 38 which takes the place of the waterproofing layer 24 shown in FIG. 4. As before, the end cap 28 is glued to the PTFE membrane by a layer of adhesive sealant 26.

EXAMPLE I

An oxygen sensor in accordance with FIG. 5, the remainder of the construction being in accordance with FIG. 4, was made as follows.

The cathode 18 was made by spreading a well mixed paste of silverised graphite catalyst and PTFE suspension (10:3 ratio of catalyst to PTFE by weight) on to 80 mesh nickel gauze. This was allowed to dry and was then cured at 200° C for one hour. The gas phase diffusion barrier 38 comprising commercial porous unsintered PTFE tape (0.008 inch thick unstretched insulating tape obtained from W. L. Gore and Associates (UK) Limited) was then pressed at 2.5 tons per square inch on to this cathode to form an integral assembly of the diffusion barrier and cathode. The pressing operation also reduced the pore-size, as previously described. Measurement showed that the ratio of permeability to diffusibility was 1.08:1 so as to give an effectively linear response.

Figure 7:
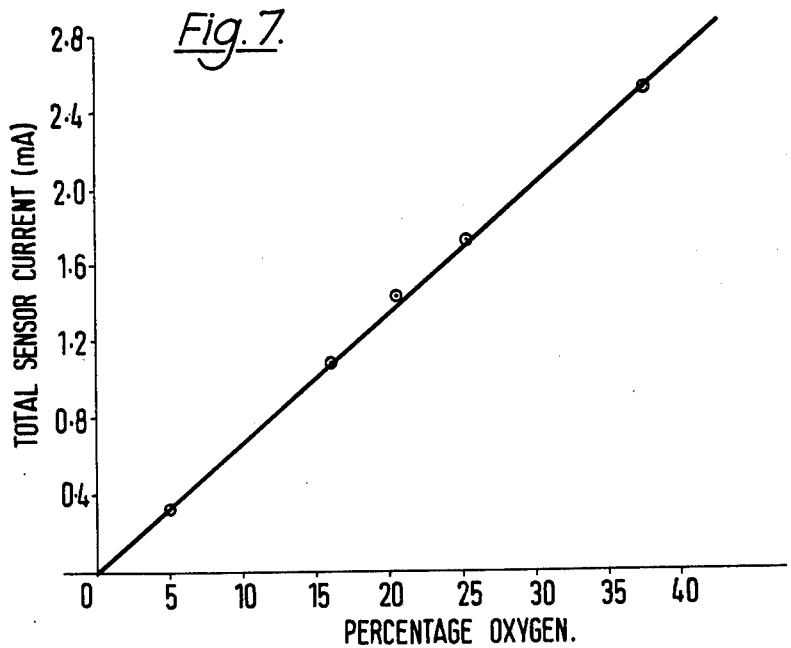
FIG. 7 is a graph showing total sensor current plotted against per centage oxygen.

The end cap 28 was made of polymethacrylate and the hole 36 had a diameter of 1 mm to restrict the diffusion area. The remaining details were as already described with reference to FIG. 4 and the electrolyte was a four molar solution of potassium carbonate. After loading with a 1 ohm resistor to bring the sensor into the limiting current region, the sensor gave a signal in ambient air of 1.4mA and responded to different oxygen concentrations in the manner shown in FIG. 7. No change in the signal in ambient air was detected over the temperature range of 0 to 50° C. The response time of the sensor for an 80% change when placed in pure nitrogen was eight seconds.

EXAMPLE II

An oxygen sensor in accordance with FIG. 4 was made up as follows.

The capillary 30 was formed through the end cap 28 by drilling a hole having a diameter of 0.34 mm and a length of 7 mm. The cathode 18 was made as in Example I and was waterproofed by means of the layer 24 by pressing unsintered porous PTFE tape of the same grade as described in Example I on to one side of the electrode, using a pressing pressure of 1 ton per square inch. This was sealed to the end cap 28 in such a way that the narrow gap denoted by the circle 31 in FIG. 4 had a depth of about 0.5 mm and a diameter of 1 cm.

The membrane 34 fitted over the outer end of the capillary 30 was formed from the same grade of porous PTFE tape referred to previously, the pore size without any pre-pressing being sufficiently small to reduce the transport of oxygen by bulk flow to an extent at which the permeability was four times greater than the diffusibility. The resulting sensor was insensitive to draughts although its response was not completely linear at oxygen concentrations above 25%. When loaded as in Example I this sensor gave a signal in ambient air of 0.90 mA. The change in signal between ambient temperature and −10° C was less than 3%. There was no detectable change in signal after the air pressure had been raised to three atmospheres.

Figure 6:
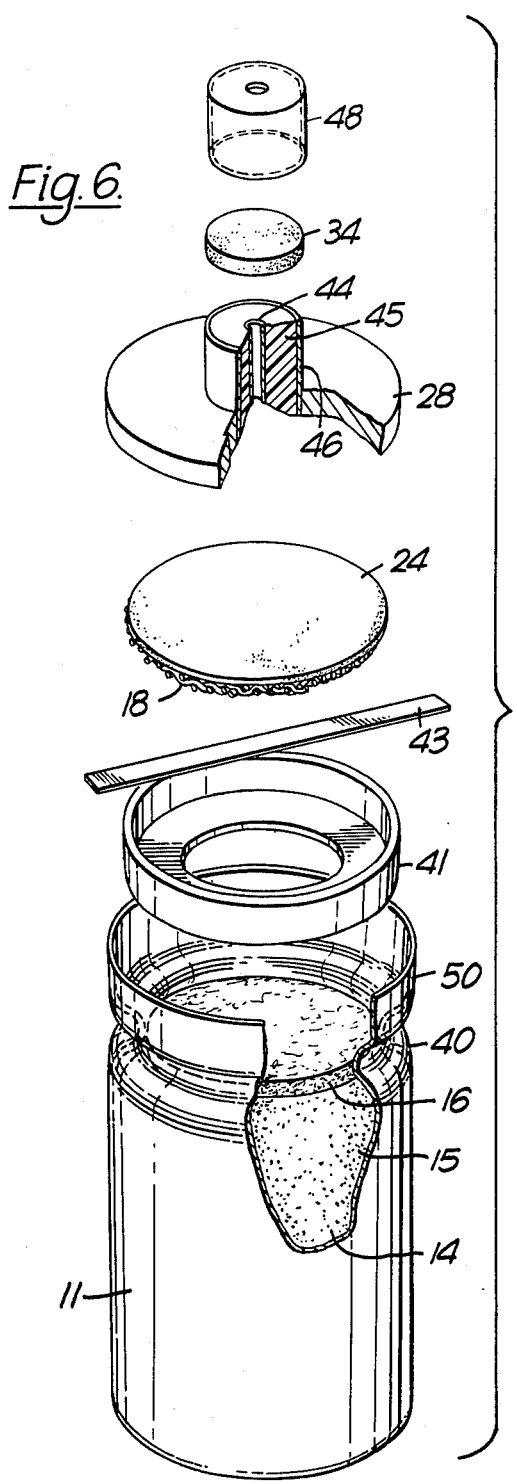
FIG. 6 is a view similar to FIG. 4 showing another form of construction of cells.

FIG. 6 shows an alternative construction of sensor, the modifications being primarily to the end cap and the cathode connection. Insofar as parts correspond to those included in FIG. 4 or FIG. 5, they are indicated by the same reference numerals. Thus a nickel-plated can 11 holds a wool lead anode 14 and electrolyte 15, on top of which is a wicking separator 16. In this construction, the can 11 is formed with a rill 40 at the level of the wicking separator 16 and the portion of the can above the rill 40 is insulated by a nylon sealing grommet 41. The assembly of cathode 18 and PTFE membrane 24 is constructed in the same way as in FIGS. 4 and 5, the membrane merely serving a water-proofing function as in FIG. 4 rather than acting as a diffusion barrier as in FIG. 5.

In this construction the cathode connection is defined by a thin silver strip 43 which is in contact with the lower face of the cathode 18 and the end portions of which extend upwardly between the grommet 41 and the end cap 28. In this modified construction, the capillary is defined by a length 44 of commercial stainless steel hypodermic tubing mounted in a thick-walled sleeve 45 of vinyl plastics which is itself contained within an outer stainless steel tube 46 fitted into the end cap 48. The capillary forms the gas-phase diffusion barrier and bulk flow effects are restricted by a membrane 34 as in FIG. 4, which is held in position by a top cap 48 fitting over the outside of the tube 46. The end 48 is held in position by crimping of the top rim 50 of the can 11.

EXAMPLE III

An oxygen sensor in accordance with FIG. 6 was made up as follows.

The lower part of the sensor was substantially in accordance with Example I except that five molar sodium hydroxide was used as electrolyte. In particular, the assembly of cathode 18 and waterproofing membrane 24 was constructed as previously. The hypodermic tubing defining the capillary 44 had a length of 5 mm, a bore of 0.3 mm and an outside diameter of 0.56 mm. The end cap 48 was made of nickel-plated mild steel which was thus in electrical connection with the cathode through the contact strip 43, as a result of pressure contact with the strip produced by the crimping of the top rim. The cathode connection was spot-welded to the top cap and the anode connection was then taken directly from the can 11.

The membrane 34 had the same characteristics as in Example II, with an open area of 0.07 square cms defined by a 3 mm diameter hole in top cap 48. When the cell was loaded as in Example I this construction of sensor gave a signal in ambient air of 1.08 mA, which was insensitive to draught.

In the example just described with reference to FIG. 6, the capillary is formed in a separate unit fitted into the end cap and this is particularly advantageous. Various modifications to the detailed construction shown in FIG. 6 are possible. Thus a thickwalled capillary of either metal or plastics may itself form the unit fitted into the end cap and this may be enclosed within an outer metal sheath to provide the additional temperature compensation referred to previously.

EXAMPLE IV

An oxygen sensor was made up exactly as in Example III, except that the membrane 34 consisted of a polycarbonate film available under the Trademark "Unipore" from BioRad Laboratories of Richmond, California, U.S.A. This film had a nominal pore size of 0.03 micrometers and a permeability less than 0.002 per cent greater than its diffusibility. This sensor gave a linear response against percentage oxygen up to 100 per cent oxygen.

Any of the sensors so far described may be combined with electronic circuits to give an audible or visible warning when the percentage of gas to be sensed reaches or falls to a particular level and, in addition, an electronic feedback circuit may be included for holding the voltage of the cell at a constant value such that the current is within the limiting current region.

We claim:

1. In an electro-chemical sensor for the measurement of concentrations of gas or vapour in accordance with the limiting current principle, said sensor comprising an electrolytic cell having a sensing electrode, a counter electrode and an intervening body of electrolyte and also including means restricting the rate of access of gas or vapour to said sensing electrode, the improvement wherein said restricting means comprises a gas-phase diffusion barrier defining at least one narrow passage for the diffusion of gas, said gasphase diffusion barrier including structure formed with capillary passage means, said structure being made of plastics material and further including an outer metal sheath being of lesser co-efficient of expansion than said plastics material of said structure.

2. In an electro-chemical sensor for the measurement of concentrations of gas or vapour in accordance with the limiting current principle, said sensor comprising an electrolytic cell having a sensing electrode, a counter electrode and an intervening body of electrolyte and also including means restricting the rate of access of gas or vapour to said sensing electrode, the improvement wherein said restricting means comprises a porous body in series with capillary passage means, the porous body and the capillary passage means cooperating to provide a gas-phase diffusion barrier defining at least one narrow passage for the diffusion of the gas being sensed so that the gas being sensed remains in the gas phase throughout the process of transport from the gas mixture under test to the sensing electrode.

3. An electro-chemical sensor according to claim 2, said sensor being adapted for use with an electro-chemically reducible gas and in which said counter electrode is a consumable metal anode which is more noble than hydrogen.

4. An electro-chemical sensor according to claim 3 in which said anode is made of lead.

5. An electro-chemical sensor according to claim 3 in which said anode is made of cadmium.

6. An electro-chemical oxygen sensor according to claim 3 in which said sensing electrode is a cathode including a nickel mesh.

7. An electro-chemical sensor according to claim 2 wherein said porous body has a permeability not more than twenty times greater than its diffusability.

8. An electro-chemical sensor according to claim 2 wherein said porous body has a permeability which is less than ten times the diffusability thereof.

9. An electro-chemical sensor according to claim 2 wherein said porous body has a permeability which is not more than 10% greater than the diffusability thereof.

10. An electro-chemical sensor according to claim 2 additionally including a porous membrane barrier in series with the restricting means and interposed between the gas mixture under test and the sensing electrode.

11. An electro-chemical sensor according to claim 2 wherein the porous body is arranged upstream from the capillary passage means along a path of flow normally followed by the gas or vapour in reaching said sensing electrode.

12. An electro-chemical sensor according to claim 2 wherein the sensing electrode together with the restricting means are fixed and sealed into a supporting housing.

* * * * *